Figure 3:
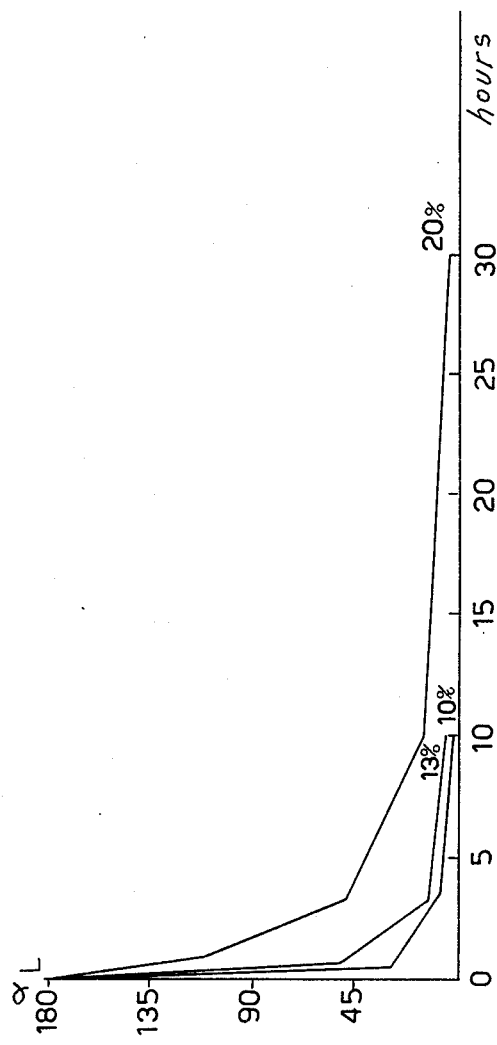

United States Patent [19]

Giobbio et al.

[11] 4,206,118

[45] Jun. 3, 1980

[54] METHOD FOR RACEMISSING D (OR L) TETRAMISOLE, AND THE RELATIVE PRODUCT

[75] Inventors: Vincenzo Giobbio; Giorgio Ornato, both of Loranzé, Italy

[73] Assignee: Marxer S.p.A., Loranzé, Italy

[21] Appl. No.: 972,263

[22] Filed: Dec. 22, 1978

[30] Foreign Application Priority Data

Aug. 24, 1978 [IT] Italy .................. 68964 A/78

[51] Int. Cl.² ............................................ C07D 277/04
[52] U.S. Cl. ...................................... 548/155; 424/270

[58] Field of Search .................................. 260/306.7 T

[56] References Cited

U.S. PATENT DOCUMENTS 3,673,206  6/1972  Bullock et al. ............... 260/306.7 T

*Primary Examiner*—Nicholas S. Rizzo
*Attorney, Agent, or Firm*—Young & Thompson

[57] ABSTRACT

D-tetramisole, or its l-tetramisole enantiomer, is racemized in solution in dimethylsulphoxide in the presence of a catalytically effective amount of potassium hydroxide.

6 Claims, 4 Drawing Figures

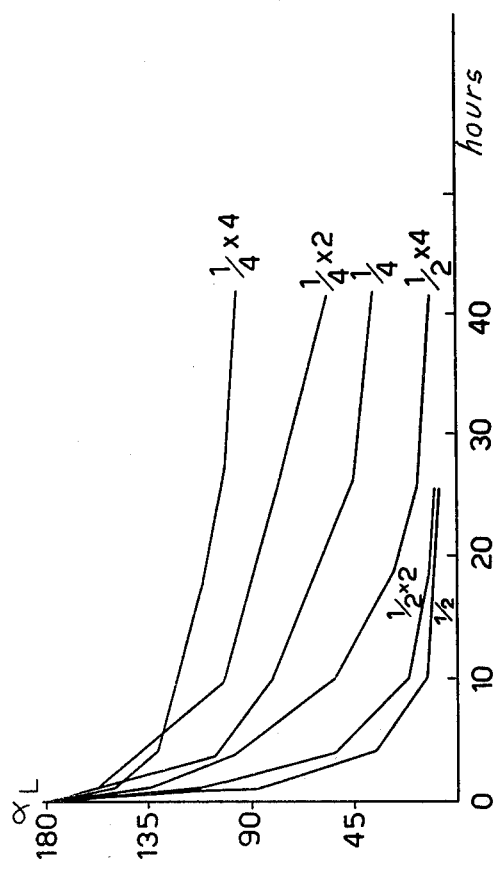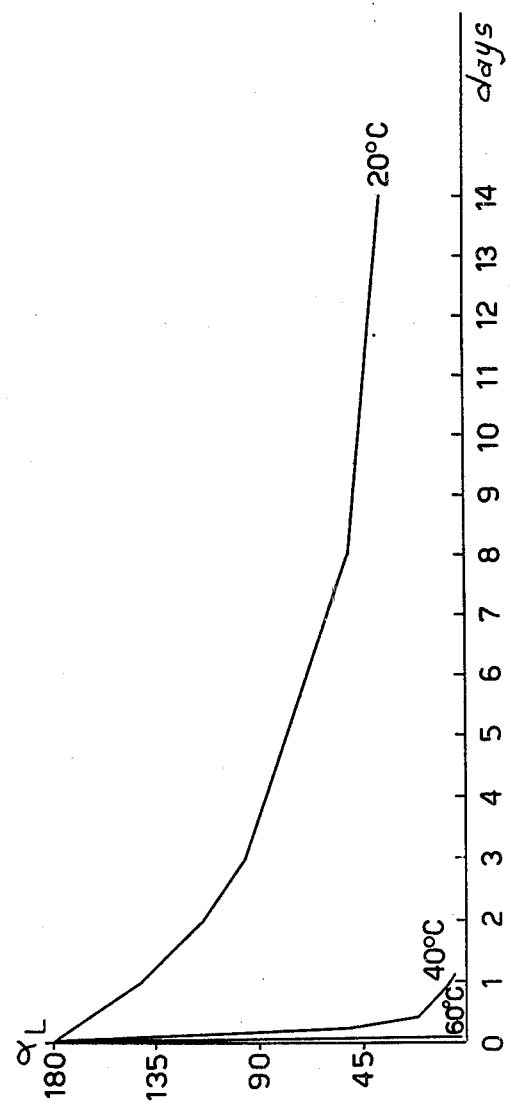

METHOD FOR RACEMISSING D (OR L) TETRAMISOLE, AND THE RELATIVE PRODUCT

Levamisole is the optically active compound l(-)6-phenyl-2,3,5,6-tetrahydro-imidazo(2,)l-b)thiazole, i.e. the levorotatory form of the raceme known as d, 1-tetramisole. The formula for this substance is as follows, from which the centre of asymmetry can be seen

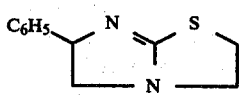

The two compounds levamisole and tetramisole are widely used as anthelmintics in the zootechnic and veterinary sectors, and are considered to be among the most effective products in this field. Furthermore, levamisole has also recently found application in the human pharmaceutical sector, namely in the treatment of tumours.

In comparing the two substances levamisole and tetramisole, it should be noted that the former represents the pharmacologically active part of the latter, and for this reason it is very important to find a practical method for separating the two optical antipodes. This separation has been performed by fractional crystallisation after salification, of the basic d, 1-tetramisole with optically active acids, the acids which have been used being d-camphosulphonic acid, Bullock, Milon, British Pat. No. 1,120,406 (1968); Bullock, Milon, British Pat. No. 1,127,852 (1968); Bullock, Milon, British Pat. No. 1,152,544 (1969); or p-tosyl-1-glutamic acid, ICI, British Pat. No. 1,169,310 (1969); or N-(p-toluenesulphonyl)-1-pyroglutamic acid, ICI, Fr. Demande No. 2,001,916 (1969).

1-dibenzoyl-tartaric acid has also been used, Dewilde, Francois, Ger. Offen. No. 2,027,030 (1970), as has 1-di-p-toluyltartaric acid, Dewilde, Francois, Ger. Offen. No. 2,020,142.

After separating the two enantiomers, the dextrorotatory form is obtained as the inactive residue, but this can be racemised to give further d, 1-tetramisole, which can in its turn be returned to the cycle for the production of further levamisole. This racemisation takes place in a basic environment in order to catalyse the reaction, and has been studied by Bullock, Milon, British Pat. No. 1,120,406 (1968).

These researchers use solvents such as dimethylformamide, dimethylsulphoxide or other similar solvents, and bases such as tertiary potassium butylate, or sodium amide, sodium hydride or other alkyloxides of alkali metals, or other alkali metal salts of amines, or other alkaline metal hydrides.

Other researchers have produced racemisation by heating d-tetramisole in dimethylformamide with ionium salts and expoxy or imino compounds, Baklieu, Asbjorn, U.S. Pat. No. 3,806,516 (1974), or with tetrabutylammonium iodide and aziridine, Baklieu, Asbjorn, Australian No. 461,447 (1974).

Others have racemised d-tetramisole in the molten state, Bullock, Hand, British Pat. No. 1,120,406.

It is important to note that the methods of the aforesaid studies and patents relative to said racemisation comprise the use of bases such as tertiary potassium butylate, sodium amide, sodium hydride, alkyloxides, alkali metal salts of amines, ionium salts, aziridine etc., substances which are characterised by being considerably dangerous to use, especially in production on an industrial scale.

It has now been surprisingly found, and constitutes substantially the object of the present invention, that the basic d-tetramisole dissolved in dimethylsulphoxide racemises in the presence of potassium hydroxide, and that this reaction takes place with times and yields which vary according to the conditions under which the operation is carried out, but which are entirely satisfactory.

In one form of this method, the basic d-tetramisole is merely dissolved in dimethylsulphoxide and solid potassium hydroxide is added.

After 48 hours of agitation it is found that racemisation of the d-tetramisole has taken place, however the degree of racemisation and the yield depend on the concentration conditions and temperature. In a preferred form of the method according to the invention, it is of overriding importance to work in the presence of a solvent in which potassium hydroxide is soluble. For this purpose, best results are obtained by using potassium hydroxide previously dissolved in methanol, ethanol or another alcohol, including a polyhydroxylic alcohol such as ethylene or propylene glycol or glycerine, or in general other solvents in which potassium hydroxide can be previously dissolved. It is also possible to use water, but this has a very negative influence on the reaction time and yield.

In this respect, all the aforesaid organic solvents which dissolve potassium hydroxide are damaging to the proper progress of the racemisation, because of which it is of fundamental importance to reduce their quantity to a minimum, whereas the presence of dimethylsulphoxide favours racemisation to an extent proportional to its concentration, and it is therefore advantageous to work in dilute solutions of d-tetramisole in dimethylsulphoxide, naturally taking account of the fact that excessive dilution may be economically disadvantageous, because of the cost of the solvent.

Temperature increase also obviously has a very favourable effect on the reaction velocity, but unfortunately also a negative effect on the quality of the raceme produced.

Finally, it should be noted that the d-tetramisole racemisation method heretofore described is also valid for racemising l-tetramisole. It is therefore apparent that the present invention considerably simplifies the d-tetramisole racemisation process, in that use is made of an economical base, namely potassium hydroxide, so also avoiding the dangers deriving from the use of the aforesaid organic bases normally used in the known art. Optimum yields are also obtained at a high purity.

Experimentally obtained diagrams are shown in the accompanying FIGS. 1 to 4, in order to clarify the influence of the variation in the reaction conditions, such as the quantity of organic solvent used for previously dissolving the potassium hydroxide, the temperature, the concentration of the other substances in solution, and the quantity of water.

The ordinate of these diagrams shows the value $\alpha_L$, which is directly proportional to the $[\alpha]_D^{25}$ for tetramisole hydrochloride in solution.

This value is obtained by withdrawing 10 ml from the solution under examination, and adding to the withdrawn portion 10 ml of water and 5 ml of 30% HCl, and finally reading the value for this new solution directly on the polarimeter.

The abscissa indicates the reaction times.

FIG. 1 shows a family of curves, each corresponding to a determined concentration ratio of potassium hydroxide/methanol, the value of this ratio being indicated on each curve, and which varies in accordance with the parameter $$[KOH\,(g)/MeOH(ml)]\cdot n, \text{ where } n=1,2,3,\ldots$$

Figure 4:
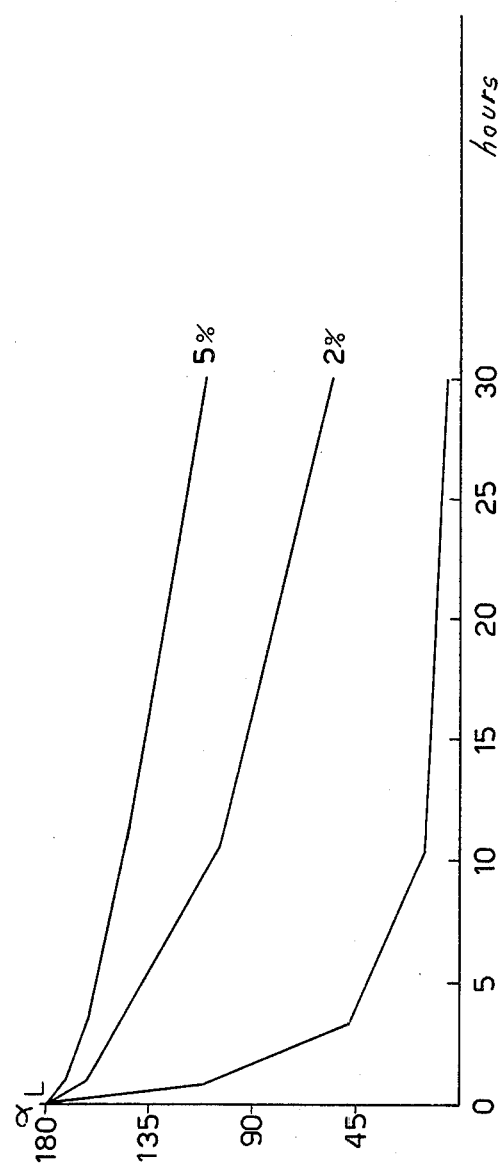

These curves are given for a tetramisole/dimethylsulphoxide concentration ratio of 20% and for a temperature of 40° C. FIG. 2 shows three curves, each for a determined temperature, for a fixed value of said parameter (KOH/MeOH·n, of ½·2 and for a tetramisole/dimethylsulphoxide concentration ratio of 20%. FIG. 3 shows three curves, each for a determined tetramisole/dimethylsulphoxide concentration value, for a fixed value of said parameter (KOH/MeOH)·n of ½·2 and for a temperature of 40° C. Finally FIG. 4 shows three curves each for a determined concentration of water in solution, for a constant (KOH/MeOH·n of ½·2, a constant temperature of 40° C. and a constant tetramisole/dimethylsulphoxide concentration ratio of 20%.

Some examples of application, which however are not to be considered limiting, are given hereinafter to clarify the present invention.

EXAMPLE 1

40 g of basic d-tetramisole are dissolved in 400 ml of dimethylsulphoxide at ambient temperature. 5 g of potassium hydroxide are dissolved separately in 10 ml of hot methanol. This second solution is added to the first, and the mixture is kept for four hours at 40° under agitation. It is then cooled to 10° C., and 400 ml of water and 400 ml of chloroform are added, and the mixture shaken for a few minutes. The chloroform phase is extracted again with a further 400 ml of water, and the tetramisole hydrochloride is precipitated from the chloroform solution by bubbling hydrogen chloride gas through it. The yield of raceme tetramisole hydrochloride is 38.6 g (82%), and the purity exceeds 98%.

EXAMPLE 2

40 g of basic d-tetramisole are dissolved in 200 ml of dimethylsulphoxide at ambient temperature, and to this is added a solution of 5g of potassium hydroxide in 10 ml of methanol.

The reaction temperature is 40° C., and the mixture is kept under agitation for 26 hours. After cooling to below 10° C., 200 ml of water and 200 ml of chloroform are added, and the mixture is shaken for a few minutes. After sedimentation and separation, the chloroform phase is again washed with 200 ml of water and separated.

The tetramisole is separated by bubbling hydrogen chloride gas through, and the yield of raceme tetramisole hydrochloride is 38 g (81%), with a purity exceeding 98%.

EXAMPLE 3

This is the same as Example 2, except that l-tetramisole is used instead of d-tetramisole.

37.5 g of the raceme are obtained, corresponding to a yield of 80%, and with a purity exceeding 98%.

EXAMPLE 4

40 g of basic l-tetramisole are dissolved in a flask in 200 ml of dimethylsulphoxide, and a separately prepared solution of 5 g of potassium hydroxide in 10 ml of methanol is added under energetic agitation. The temperature is raised to 60°, and the mixture is kept under agitation for 2 hours. It is cooled to below 10° C., 200 ml of water and 200 ml of chloroform are added, and the mixture well shaken. Two phases separate on leaving the mixture to stand. The chloroform phase is washed with 200 ml of water, and after separation the organic phase is precipitated with hydrogen chloride gas.

The raceme tetramisole hydrochloride obtained in this manner weighs 36.2 g, the yield is 77% and the purity exceeds 98%.

We claim:

1. A method for racemizing tetramisole, comprising contacting tetramisole in solution in dimethylsulphoxide with a catalytically effective amount of potassium hydroxide.

2. A method as claimed in claim 1, in which said tetramisole is d-tetramisole.

3. A method as claimed in claim 1, in which said tetramisole is l-tetramisole.

4. A method as claimed in claim 1, and adding said potassium hydroxide in solid state directly to said solution.

5. A method as claimed in claim 1, and adding said potassium hydroxide in solution to the first-mentioned said solution.

6. A method as claimed in claim 1, in which said tetramisole is present in an amount of 5 to 20% by weight of said dimethylsulphoxide, said potassium hydroxide being present in an amount between 5 and 100% by weight of said tetramisole.

* * * * *